United States Patent
Schafer et al.

(10) Patent No.: US 9,480,676 B2
(45) Date of Patent: Nov. 1, 2016

(54) USE OF PDE4 INHIBITORS AND COMBINATIONS THEREOF FOR THE TREATMENT OF CYSTIC FIBROSIS

(71) Applicant: Celgene Corporation, Summit, NJ (US)

(72) Inventors: Peter H. Schafer, Belle Mead, NJ (US); Shimon Korish, Randolph, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/712,595

(22) Filed: May 14, 2015

(65) Prior Publication Data

US 2015/0328187 A1    Nov. 19, 2015

Related U.S. Application Data

(60) Provisional application No. 61/993,467, filed on May 15, 2014.

(51) Int. Cl.
| | | |
|---|---|---|
| *A61K 31/47* | (2006.01) | |
| *A61K 31/4035* | (2006.01) | |
| *A61K 45/06* | (2006.01) | |
| *A61K 31/443* | (2006.01) | |

(52) U.S. Cl.
CPC ......... *A61K 31/4035* (2013.01); *A61K 31/443* (2013.01); *A61K 31/47* (2013.01); *A61K 45/06* (2013.01)

(58) Field of Classification Search
None
See application file for complete search history.

(56) References Cited

U.S. PATENT DOCUMENTS 6,962,940 B2 *   11/2005   Muller ............... A61K 31/4035
                                                        514/417

FOREIGN PATENT DOCUMENTS

AU          2006200033 A1 *   2/2006

OTHER PUBLICATIONS

Silva, A., Mini-Reviews in Medicinal Chemistry, 2005, vol. 5, pp. 893-014.*
Liu, S. et al., J. Pharmacol. Exp. Thera 2005 vol. 314 pp. 846-854.*
Pettit, R. Ann Pharmacotherapy 2012 vol. 46 pp. 1065-1074.*
Char, J. et al PLOS ONE 2014 vol. 9 pp. 1-16.*

* cited by examiner

*Primary Examiner* — Heidi Reese
(74) *Attorney, Agent, or Firm* — Jones Day

(57) ABSTRACT

Methods of treating cystic fibrosis by administering a PDE4 inhibitor in combination with one or more cystic fibrosis transmembrane conductance regulator (CFTR) potentiators, including ivacaftor, and/or one or more CFTR correctors, including lumacaftor. Pharmaceutical compositions, dosage forms, and kits suitable for use in methods of the invention are also disclosed.

17 Claims, No Drawings

USE OF PDE4 INHIBITORS AND COMBINATIONS THEREOF FOR THE TREATMENT OF CYSTIC FIBROSIS

This application claims priority to U.S. Provisional Patent Application No. 61/993,467, filed May 15, 2014, the entirety of which is incorporated herein by reference.

1. FIELD

Provided herein are methods of treating cystic fibrosis by administering a PDE4 inhibitor in combination with one or more cystic fibrosis transmembrane conductance regulator (CFTR) potentiators, including ivacaftor, and/or one or more CFTR correctors, including lumacaftor.

2. BACKGROUND

Cystic fibrosis is a hereditary life-threatening disorder that causes severe lung damage and nutritional deficiencies. Cystic fibrosis ("CF") is caused by defects in the cystic fibrosis transmembrane conductance regulator (CFTR) protein, which results from mutations in the CFTR gene. CFTR protein channels regulate chloride ion and water flow in and out of a cell. The transport of salt ions and water keeps the lungs and other organs hydrated. In people with certain CFTR gene mutations, the CFTR protein channels do not function properly, resulting in an imbalance of salt and water. This leads to the buildup of abnormally thick and sticky mucus in the lungs and other organs, which often become infected.

CFTR is activated by cAMP elevation and PKA activation, via PDE3 or PDE4 inhibition. Thus, a cAMP elevating agent, such as a PDE4 inhibitor, would be useful in the treatment of CF by activating CFTR. Roflumilast is an example of a PDE4 inhibitor which has shown activating effects on CFTR. See Liu, S. et al., *J. Pharmacol Exp Ther.*, 2005, 314(2): 846-54.

Ivacaftor (KALYDECO™ or VX-770) is a CFTR potentiator indicated for the treatment of CF in patients having a G551D mutation in the CFTR gene. See WO 2011/050325 A1. A very small percentage of the CF patient population has the G551D mutation, approximately 4% or 1200 patients in the United States. Another mutation in the CF gene which occurs in approximately 3% of CF patients in the United States is the R1 17H mutation. Ivacaftor is not approved for CF patients having more common mutations in the CFTR gene, such as the delF508 mutation. The delF508 mutation impairs the folding, stability and gating of CFTR protein. CFTR corrector compounds, such as lumacaftor (VX-809) or Corr-4a, can partially alleviate the folding defect. Still, there is an unmet need to find an effective treatment of CF, including in patients having CFTR mutations other than the G551D mutation.

3. SUMMARY

Provided herein are methods of treating cystic fibrosis by administering a PDE4 inhibitor, or a pharmaceutically acceptable salt, hydrate, solvate, clathrate, prodrug, or polymorph thereof in combination with one or more cystic fibrosis transmembrane conductance regulator (CFTR) potentiators and/or one or more CFTR correctors. In some embodiments, the CFTR potentiator is ivacaftor. In some embodiments, the CFTR corrector is lumacaftor.

In some embodiments, the PDE4 inhibitor is N-(2-(1-(3-ethoxy-4-methoxyphenyl)-2-(methylsulfonyl)ethyl)-1,3-dioxoisoindolin-4-yl)acetamide, or an enantiomer thereof, or a pharmaceutically acceptable prodrug, metabolite, polymorph, salt, solvate or clathrate thereof. In one embodiment, the PDE4 inhibitor is (S)—N-(2-(1-(3-ethoxy-4-methoxyphenyl)-2-(methylsulfonyl)ethyl)-1,3-dioxoisoindolin-4-yl)acetamide, or a pharmaceutically acceptable prodrug, metabolite, polymorph, salt, solvate or clathrate thereof. In another embodiment, the PDE4 inhibitor is (R)—N-(2-(1-(3-ethoxy-4-methoxyphenyl)-2-(methylsulfonyl)ethyl)-1,3-dioxoisoindolin-4-yl)acetamide, or a pharmaceutically acceptable prodrug, metabolite, polymorph, salt, solvate or clathrate thereof.

In other embodiments, the PDE4 inhibitor is (S)—N-(2-(1-(3-ethoxy-4-methoxyphenyl)-2-(methylsulfonyl)ethyl)-3-oxoisoindolin-4-yl)cyclopropanecarboxamide, or a pharmaceutically acceptable prodrug, metabolite, polymorph, salt, solvate or clathrate thereof.

In one embodiment, provided herein is a method of treating cystic fibrosis by administering an effective amount of (S)—N-(2-(1-(3-ethoxy-4-methoxyphenyl)-2-(methylsulfonyl)ethyl)-1,3-dioxoisoindolin-4-yl)acetamide in combination or alternation with an effective amount of ivacaftor and/or an effective amount of lumacaftor.

In one embodiment, provided herein is a method of treating cystic fibrosis by administering an effective amount of (S)—N-(2-(1-(3-ethoxy-4-methoxyphenyl)-2-(methylsulfonyl)ethyl)-3-oxoisoindolin-4-yl)cyclopropanecarboxamide in combination or alternation with an effective amount of ivacaftor and/or an effective amount of lumacaftor.

4. DETAILED DESCRIPTION

4.1. Combination Therapies Comprising PDE4 Inhibitors for the Treatment of Cystic Fibrosis Provided herein are methods of treating cystic fibrosis by administering a PDE4 inhibitor, or a pharmaceutically acceptable salt, hydrate, solvate, clathrate, prodrug, or polymorph thereof in combination with one or more cystic fibrosis transmembrane conductance regulator (CFTR) potentiators and/or one or more CFTR correctors. A PDE4 inhibitor, or a pharmaceutically acceptable salt, hydrate, solvate, clathrate, prodrug, or polymorph thereof as defined herein, in combination with one or more cystic fibrosis transmembrane conductance regulator (CFTR) potentiators and/or one or more CFTR correctors can be used as a medicament. In some embodiments, the CFTR potentiator is ivacaftor. In some embodiments, the CFTR corrector is lumacaftor.

In some embodiments, the PDE4 inhibitor is N-(2-(1-(3-ethoxy-4-methoxyphenyl)-2-(methylsulfonyl)ethyl)-1,3-dioxoisoindolin-4-yl)acetamide, an enantiomer thereof, or mixtures of enantiomers thereof "Compound A" as used herein refers to N-(2-(1-(3-ethoxy-4-methoxyphenyl)-2-(methylsulfonyl)ethyl)-1,3-dioxoisoindolin-4-yl)acetamide.

In some embodiments, the PDE4 inhibitor is (S)—N-(2-(1-(3-ethoxy-4-methoxyphenyl)-2-(methylsulfonyl)ethyl)-1,3-dioxoisoindolin-4-yl)acetamide, which is the (+) enantiomer of 2-[1-(3-ethoxy-4-methoxyphenyl)-2-methylsulfonylethyl]-4-acetylaminoisoindoline-1,3-dione, also known as Apremilast, or a pharmaceutically acceptable prodrug, metabolite, polymorph, salt, solvate or clathrate thereof. "Compound A1" as used herein refers to (S)—N-(2-(1-(3-ethoxy-4-methoxyphenyl)-2-(methylsulfonyl) ethyl)-1,3-dioxoisoindolin-4-yl)acetamide. Without being limited by theory, the (+) enantiomer of 2-[1-(3-ethoxy-4-methoxyphenyl)-2-methylsulfonylethyl]-4-acetylaminoisoindoline-1,3-dione is believed to be (S)—N-(2-(1-(3- ethoxy-4-methoxyphenyl)-2-(methylsulfonyl)ethyl)-1,3-dioxoisoindolin-4-yl)acetamide, which has the following structure:

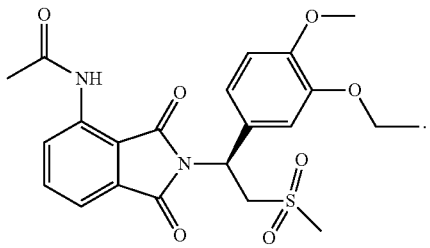

(A1)

In some embodiments, the PDE4 inhibitor is (R)—N-(2-(1-(3-ethoxy-4-methoxyphenyl)-2-(methylsulfonyl)ethyl)-1,3-dioxoisoindolin-4-yl)acetamide, which is the (−) enantiomer of 2-[1-(3-ethoxy-4-methoxyphenyl)-2-methylsulfonylethyl]-4-acetylaminoisoindoline-1,3-dione. "Compound A2" as used herein refers to (R)—N-(2-(1-(3-ethoxy-4-methoxyphenyl)-2-(methylsulfonyl)ethyl)-1,3-dioxoisoindolin-4-yl)acetamide. As disclosed herein, compounds A, A1 and A2 also refer to the compound of formula (I):

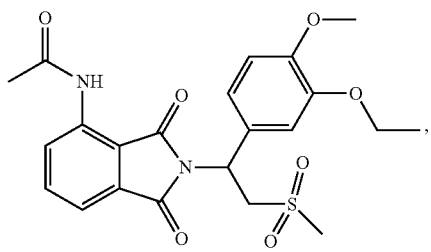 [SMILES: CCOc1cc(C(CS(C)(=O)=O)N2C(=O)c3cccc(NC(C)=O)c3C2=O)ccc1OC]

or to the compound of formula (III):

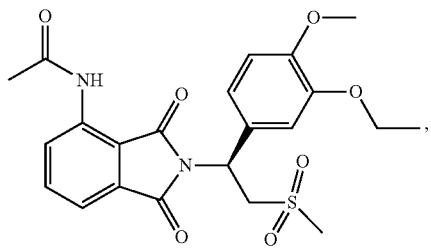 [SMILES: CCOc1cc([C@@H](CS(C)(=O)=O)N2C(=O)c3cccc(NC(C)=O)c3C2=O)ccc1OC]

or to the compound of formula (IV):

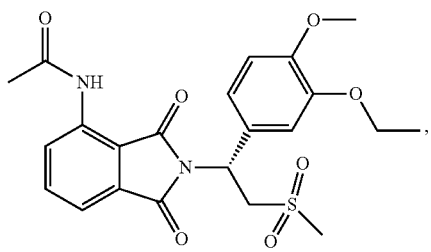 [SMILES: CCOc1cc([C@H](CS(C)(=O)=O)N2C(=O)c3cccc(NC(C)=O)c3C2=O)ccc1OC]

respectively.

Compounds A, A1 and A2 can be prepared according to methods disclosed in U.S. Pat. No. 6,962,940, titled "(+)-2-[1-(3-Ethoxy-4-methoxyphenyl)-2-methylsulfonylethyl]-4-acetylaminoisoindoline-1,3-dione: Methods Of Using And Compositions Thereof," or U.S. Patent Publication No. 2010/0168475, each of which are incorporated herein by reference. Generally, racemic 2-[1-(3-ethoxy-4-methoxyphenyl)-2-methylsulfonylethyl]-4-acetylaminoisoindoline-1,3-dione can be readily prepared using the methods described in U.S. Pat. No. 6,020,358, which is incorporated herein by reference. The corresponding (+) and (−) enantiomers can be isolated from the racemic compound by techniques known in the art. Examples include, but are not limited to, the formation of chiral salts and the use of chiral or high performance liquid chromatography "HPLC" and the formation and crystallization of chiral salts. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N.Y., 1962); and Wilen, S. H., *Tables of Resolving Agents and Optical Resolutions* p. 268 (E. L. Eliel, Ed., Univ. of Notre Dame Press, Notre Dame, Ind., 1972).

In a specific method, the (+) enantiomer of 2-[1-(3-ethoxy-4-methoxyphenyl)-2-methylsulfonylethyl]-4-acetylaminoisoindoline-1,3-dione is synthesized from 3-acetamidophthalic anhydride and a chiral amino acid salt of (S)-2-(3-ethoxy-4-methoxyphenyl)-1-(methylsulphonyl)-eth-2-ylamine. Chiral amino acid salts of (S)-2-(3 ethoxy-4-methoxyphenyl)-1-(methylsulphonyl)-eth-2-ylamine include, but are not limited to salts formed with the L isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, 4-aminobutyric acid, 2-aminoisobutyric acid, 3-aminopropionic acid, ornithine, norleucine, norvaline, hydroxyproline, sarcosine, citrulline, cysteic acid, t-butylglycine, t-butylalanine, phenylglycine, cyclohexylalanine, and N-acetyl-L-leucine. A specific chiral amino acid salt is (S)-2-(3-ethoxy-4-methoxyphenyl)-1-(methylsulphonyl)-eth-2-ylamine N-acetyl-L-leucine salt, which is resolved from 2-(3-ethoxy-4-methoxyphenyl)-1-(methylsulphonyl)-eth-2-ylamine and N-acetyl-L-leucine in methanol.

In some embodiments, Compound A, A1, A2, or B act as a PDE4 inhibitor, or a pharmaceutically acceptable salt, hydrate, solvate, clathrate, prodrug, or polymorph thereof as defined herein, in combination with one or more cystic fibrosis transmembrane conductance regulator (CFTR) potentiators and/or one or more CFTR correctors can be used in a method of treating cystic fibrosis.

In some embodiments, the PDE4 inhibitor is Compound B, which refers to enantiomerically pure cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide, in combination with a second active agent. As referred herein, Compound B is also named as the compound of formula (II).

Without being limited by theory, Compound B is believed to be (S)—N-(2-(1-(3-ethoxy-4-methoxyphenyl)-2-(methylsulfonyl)ethyl)-3-oxoisoindolin-4-yl)cyclopropanecarboxamide, which has the following structure:

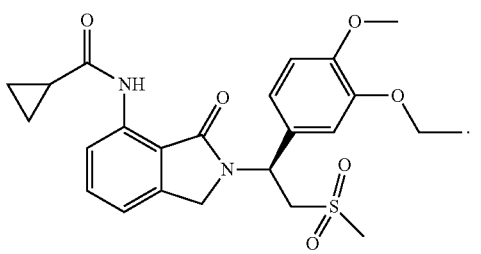

(B)

In one embodiment, provided herein is a method of treating cystic fibrosis by administering an effective amount of N-(2-(1-(3-ethoxy-4-methoxyphenyl)-2-(methylsulfonyl)ethyl)-1,3-dioxoisoindolin-4-yl)acetamide in combination or alternation with an effective amount of ivacaftor and/or lumacaftor.

In one embodiment, provided herein is a method of treating cystic fibrosis by administering an effective amount of N-(2-(1-(3-ethoxy-4-methoxyphenyl)-2-(methylsulfonyl)ethyl)-1,3-dioxoisoindolin-4-yl)acetamide in combination or alternation with an effective amount of ivacaftor or lumacaftor.

In one embodiment, provided herein is a method of treating cystic fibrosis by administering an effective amount of N-(2-(1-(3-ethoxy-4-methoxyphenyl)-2-(methylsulfonyl)ethyl)-1,3-dioxoisoindolin-4-yl)acetamide in combination or alternation with an effective amount of ivacaftor and lumacaftor.

In one embodiment, provided herein is a method of treating cystic fibrosis by administering an effective amount of (S)—N-(2-(1-(3-ethoxy-4-methoxyphenyl)-2-(methylsulfonyl)ethyl)-1,3-dioxoisoindolin-4-yl)acetamide in combination or alternation with an effective amount of ivacaftor and/or lumacaftor.

In one embodiment, provided herein is a method of treating cystic fibrosis by administering an effective amount of (S)—N-(2-(1-(3-ethoxy-4-methoxyphenyl)-2-(methylsulfonyl)ethyl)-1,3-dioxoisoindolin-4-yl)acetamide in combination or alternation with an effective amount of ivacaftor or lumacaftor.

In one embodiment, provided herein is a method of treating cystic fibrosis by administering an effective amount of (S)—N-(2-(1-(3-ethoxy-4-methoxyphenyl)-2-(methylsulfonyl)ethyl)-1,3-dioxoisoindolin-4-yl)acetamide in combination or alternation with an effective amount of ivacaftor and lumacaftor.

In one embodiment, provided herein is a method of treating cystic fibrosis by administering an effective amount of (R)—N-(2-(1-(3-ethoxy-4-methoxyphenyl)-2-(methylsulfonyl)ethyl)-1,3-dioxoisoindolin-4-yl)acetamide in combination or alternation with an effective amount of ivacaftor and/or lumacaftor.

In one embodiment, provided herein is a method of treating cystic fibrosis by administering an effective amount of (R)—N-(2-(1-(3-ethoxy-4-methoxyphenyl)-2-(methylsulfonyl)ethyl)-1,3-dioxoisoindolin-4-yl)acetamide in combination or alternation with an effective amount of ivacaftor or lumacaftor.

In one embodiment, provided herein is a method of treating cystic fibrosis by administering an effective amount of (R)—N-(2-(1-(3-ethoxy-4-methoxyphenyl)-2-(methylsulfonyl)ethyl)-1,3-dioxoisoindolin-4-yl)acetamide in combination or alternation with an effective amount of ivacaftor and lumacaftor.

In one embodiment, provided herein is a method of treating cystic fibrosis by administering an effective amount of (S)—N-(2-(1-(3-ethoxy-4-methoxyphenyl)-2-(methylsulfonyl)ethyl)-3-oxoisoindolin-4-yl)cyclopropanecarboxamide in combination or alternation with an effective amount of ivacaftor and/or lumacaftor.

In one embodiment, provided herein is a method of treating cystic fibrosis by administering an effective amount of (S)—N-(2-(1-(3-ethoxy-4-methoxyphenyl)-2-(methylsulfonyl)ethyl)-3-oxoisoindolin-4-yl)cyclopropanecarboxamide in combination or alternation with an effective amount of ivacaftor or lumacaftor.

In one embodiment, provided herein is a method of treating cystic fibrosis by administering an effective amount of (S)—N-(2-(1-(3-ethoxy-4-methoxyphenyl)-2-(methylsulfonyl)ethyl)-3-oxoisoindolin-4-yl)cyclopropanecarboxamide in combination or alternation with an effective amount of ivacaftor and lumacaftor.

In some embodiments, the CF (Cystic Fibrosis) patient to be treated exhibits the G551D mutation in the CFTR gene. In some embodiments, the CF patient to be treated exhibits the delF508 mutation in the CFTR gene. In some embodiments, the CF patient to be treated exhibits the R117H mutation in the CFTR gene.

In some embodiments, one or more of the active agents are administered orally.

In some embodiments, one or more of the active agents are administered orally in a tablet or in capsule form.

In some embodiments, ivacaftor is administered orally in an amount of 150 mg twice per day. In some embodiments, ivacaftor is administered orally in an amount of 250 mg twice per day.

In some embodiments, lumacaftor is administered orally in an amount of 400 mg twice per day. In some embodiments, lumacaftor is administered orally in an amount of 600 mg twice per day.

In some embodiments, one or more of the active agents as defined herein are administered by inhalation.

In some embodiments, the therapeutically effective amount of Compound A, A1, A2, or B to be administered to a patient in need is about 1, 5, 10, 20, 25 or 30 mg per day. In some embodiment, the therapeutically effective amount of Compound A, A1, A2, or B to be administered to a patient in need is about 1 mg per day. In some embodiment, the therapeutically effective amount of Compound A, A1, A2, or B to be administered to a patient in need is about, 5 mg per day. In some embodiment, the therapeutically effective amount of Compound A, A1, A2, or B to be administered to a patient in need is about 10 mg per day. In some embodiment, the therapeutically effective amount of Compound A, A1, A2, or B to be administered to a patient in need is about 20 mg per day. In some embodiment, the therapeutically effective amount of Compound A, A1, A2, or B to be administered to a patient in need is about 25 mg per day. In some embodiment, the therapeutically effective amount of Compound A, A1, A2, or B to be administered to a patient in need is about 30 mg per day.

4.2. Definitions

As used herein, the term "Compound A" refers to N-(2-(1-(3-ethoxy-4-methoxyphenyl)-2-(methylsulfonyl)ethyl)-1,3-dioxoisoindolin-4-yl)acetamide, also known as 2-[1-(3-ethoxy-4-methoxyphenyl)-2-methylsulfonylethyl]-4-acetylaminoisoindoline-1,3-dione, also referred to "the compound of formula (I)".

As used herein, the term "Compound A1" refers to an enantiomerically pure form of 2-[1-(3-ethoxy-4-methoxyphenyl)-2-methylsulfonylethyl]-4-acetylaminoisoindoline-1,3-dione, also referred to "the compound of formula (III), also known as Apremilast, and which when dissolved in methanol rotates plane polarized light in the (+) direction. Without being limited by theory, Compound A1 is believed to be (S)—N-(2-(1-(3-ethoxy-4-methoxyphenyl)-2-(methylsulfonyl)ethyl)-1,3-dioxoisoindolin-4-yl)acetamide, which has the following structure:

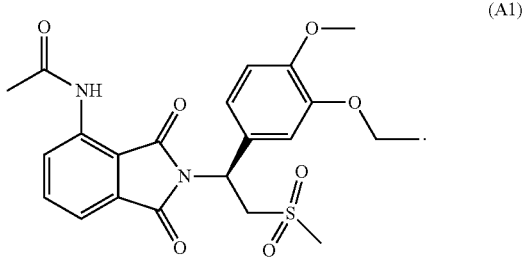 [SMILES: CCOc1cc([C@@H](CS(C)(=O)=O)N2C(=O)c3cccc(NC(C)=O)c3C2=O)ccc1OC]

(A1)

Enzyme assay data using purified PDE4 enzyme from U937 human monocytic cells indicate that Compound A1 has a PDE4 $IC_{50}$ of about 74 nM.

As used herein, the term "Compound A2", also referred to as "the Compound of formula (IV)", refers to an enantiomerically pure form of 2-[1-(3-ethoxy-4-methoxyphenyl)-2-methylsulfonylethyl]-4-acetylaminoisoindoline-1,3-dione, which when dissolved in methanol rotates plane polarized light in the (−) direction. Without being limited by theory, Compound A2 is believed to be (R)—N-(2-(1-(3-ethoxy-4-methoxyphenyl)-2-(methylsulfonyl)ethyl)-1,3-dioxoisoindolin-4-yl)acetamide.

As used herein, the term "Compound B", referred to as "the Compound of formula (II)", refers to enantiomerically pure cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide. Without being limited by theory, Compound B is believed to be (S)—N-(2-(1-(3-ethoxy-4-methoxyphenyl)-2-(methylsulfonyl)ethyl)-3-oxoisoindolin-4-yl)cyclopropanecarboxamide, which has the following structure:

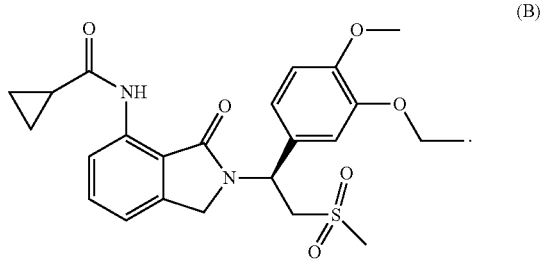 [SMILES: CCOc1cc([C@@H](CS(C)(=O)=O)N2Cc3cccc(NC(=O)C4CC4)c3C2=O)ccc1OC]

(B)

Enzyme assay data using purified PDE4 enzyme from U937 human monocytic cells indicate that Compound B has a PDE4 $IC_{50}$ of about 100 nM.

As used herein and unless otherwise indicated, the term "pharmaceutically acceptable salt" includes, but is not limited to, salts prepared from pharmaceutically acceptable non-toxic acids or bases including inorganic acids and bases and organic acids and bases. Suitable pharmaceutically acceptable base addition salts include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts.

As used herein and unless otherwise indicated, the term "hydrate" means a compound provided herein or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate and the like).

As used herein and unless otherwise specified, the term "crystal forms," "crystalline forms" and related terms herein refer to solid forms that are crystalline. Crystal forms include single-component crystal forms and multiple-component crystal forms, and include, but are not limited to, polymorphs, solvates, hydrates, and/or other molecular complexes. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

As used herein and unless otherwise specified, the terms "polymorphs," "polymorphic forms" and related terms herein, refer to two or more crystal forms that consist essentially of the same molecule, molecules, and/or ions. Like different crystal forms, different polymorphs may have different physical properties such as, e.g., melting temperature, heat of fusion, solubility, dissolution properties and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (e.g., one polymorph might be more likely to form solvates or might be difficult to filter and wash free of impurities, and particle shape and size distribution might be different between polymorphs).

As used herein and unless otherwise specified, the term "prodrug" means a derivative of a compound that can hydrolyze, oxidize, or otherwise react under biological conditions (in vitro or in vivo) to provide the compound. Examples of prodrugs include, but are not limited to, derivatives and metabolites of (+)-2-[1-(3-ethoxy-4-methoxyphenyl)-2-methylsulfonylethyl]-4-acetylaminoisoindoline-1,3-dione that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by 1 *Burger's Medicinal Chemistry and Drug Discovery,* 172-178, 949-982 (Manfred E. Wolff ed., 5th ed. 1995).

As used herein, and unless otherwise specified, the term "enantiomer," "isomer" or "stereoisomer" encompasses all enantiomerically/stereomerically pure and enantiomerically/stereomerically enriched compounds provided herein.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure, when the compound contains greater than or equal to 80%, 85%, 90%, 95%, 98% or 99% of one stereoisomer, and about 20%, 15%, 10%, 5%, 2%, 1% or less of the counter stereoisomer. "Substantially free of its (−) enantiomer" is encompassed by the term stereomerically pure or enantiomerically pure.

As used herein, term "adverse effect" includes, but is not limited to gastrointestinal, renal and hepatic toxicities, leukopenia, increases in bleeding times due to, e.g., thrombocytopenia, and prolongation of gestation, nausea, vomiting, somnolence, asthenia, dizziness, teratogenicity, extra-pyramidal symptoms, akathisia, cardiotoxicity including cardiovascular disturbances, inflammation, male sexual dysfunction, and elevated serum liver enzyme levels. The term "gastrointestinal toxicities" includes but is not limited to gastric and intestinal ulcerations and erosions. The term "renal toxicities" includes but is not limited to such conditions as papillary necrosis and chronic interstitial nephritis.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, the term "patient" refers to a mammal, particularly a human. In some embodiments, the patient is a female. In further embodiments, the patient is a male. In further embodiments, the patient is a child.

As used herein, and unless otherwise specified, the terms "treat," "treating" and "treatment" contemplate an action that occurs while a patient is suffering from the specified disease or disorder, which reduces the severity or symptoms of the disease or disorder, or retards or slows the progression or symptoms of the disease or disorder.

4.3. Methods of Treatment

Provided herein are methods of treating cystic fibroses (also named "CF" herein) which comprise administering to a patient in need of such treatment a therapeutically effective amount of Compound A (the compound of formula (I)) or Compound B (the compound of formula (II)), or a pharmaceutically acceptable prodrug, metabolite, polymorph, salt, solvate or clathrate thereof, in combination with one or more cystic fibrosis transmembrane conductance regulator (CFTR) potentiators, including ivacaftor, and/or one or more CFTR correctors, including lumacaftor. In some embodiments, the salt or solvate of Compound A, Compound A1 (the compound of formula (III)), Compound A2 (the compound of formula (IV)) or Compound B, is used. In other embodiments, the free base of the compound is used.

Methods provided herein comprise administering one of Compound A, Compound A1, Compound A2 or Compound B, or a pharmaceutically acceptable prodrug, metabolite, polymorph, salt, solvate or clathrate of thereof, after the onset of symptoms of CF. In some embodiments, provided herein comprise administering either one of Compound A1 or Compound B, substantially free of its (−) enantiomer, or a pharmaceutically acceptable prodrug, metabolite, polymorph, salt, solvate or clathrate of thereof, after the onset of symptoms of CF. Symptoms of CF include, but are not limited to, chronic cough and/or wheezing, gagging and/or vomiting, disturbed sleep, chronic pulmonary infections, pulmonary hypertension, pulmonary muscular hypertrophy, ventricular hypertrophy, nasal polyposis, sinusitis, cyanosis, hemoptysis, collapsed lung and pulmonary deterioration. Symptoms of pancreatic insufficiency may also result from CF, including but not limited to abdominal pain, diarrhea, abnormal stools, abdominal protruberance, poor growth patter with decreased subcutaneous tissue and/or muscle mass.

Methods provided herein also include inhibiting or averting symptoms of CF as well as addressing the disease itself, prior to the onset of symptoms by administering one of Compound A, Compound A1, Compound A2 or Compound B, or a pharmaceutically acceptable prodrug, metabolite, polymorph, salt, solvate or clathrate thereof in combination with one or more cystic fibrosis transmembrane conductance regulator (CFTR) potentiators, including ivacaftor, and/or one or more CFTR correctors, including lumacaftor.

The magnitude of a therapeutic dose of a particular active ingredient in the acute or chronic management of CF will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors.

In general, the recommended daily dose ranges described herein lie within the range of from about 0.1 mg to about 1,000 mg per day, given as a single once-a-day dose or as divided doses throughout a day. More specifically, the daily dose may be administered once, daily in equally divided doses. More specifically, the daily dose may be administered twice daily in equally divided doses. More specifically, the daily dose may be administered three times daily in equally divided doses. More specifically, the daily dose may be administered four times daily in equally divided doses.

Specifically, a daily dose range may be from about 1 mg to about 500 mg per day, more specifically, between about 10 mg and about 200 mg per day. Specifically, the daily dose may be administered in 1 mg, 5 mg, 6.25 mg, 10 mg, 15 mg, 20 mg, 25 mg, 30 mg, 50 mg, 100 mg, 150 mg, 200 mg, 250 mg, 300 mg, 350 mg, 400 mg, 450 mg, or 500 mg dosage forms (Q.D. or B.I.D.). In managing the patient, the therapy may be initiated at a lower dose, perhaps about 1 mg to about 25 mg, and increased if necessary up to about 200 mg to about 1,000 mg per day as either a single dose or divided doses, depending on the patient's global response. In further embodiments, the daily dose of Compound A, Compound A1, Compound A2 or Compound B is from about 0.01 mg to about 100 mg per kg of a body weight of a patient. In further embodiments, the daily dose of Compound A is from about 0.01 mg to about 100 mg per kg of a body weight of a patient. In further embodiments, the daily dose of Compound A1 is from about 0.01 mg to about 100 mg per kg of a body weight of a patient. In further embodiments, the daily dose of Compound A2 is from about 0.01 mg to about 100 mg per kg of a body weight of a patient. In further embodiments, the daily dose of Compound B is from about 0.01 mg to about 100 mg per kg of a body weight of a patient. In some embodiments, the daily dose of the chosen compound is about 1 mg/kg, 5 mg/kg, 6.25 mg/kg, 10 mg/kg or 25 mg/kg. In certain embodiments, the therapeutically effective amount of the first active agent as provided herein is about 1, 5, or 25 mg per kg of a body weight of the patient per day and the therapeutically effective amount of the additional active agent as provided herein is about 1, 5, or 6.25 mg per kg of a body weight of the patient per day.

The recommended daily dose of CFTR potentiator, e.g., ivacaftor, or CFTR corrector, e.g., lumacaftor, described herein lie within the range of from about 0.1 mg to about 1,000 mg per day, given as a single once-a-day dose or as divided doses throughout a day. More specifically, the daily dose may be administered once, twice, three times, or four times daily in equally divided doses. Specifically, a daily dose range may be from about 1 mg to about 1000 mg per day, more specifically, between about 10 mg and about 800 mg per day. Specifically, the daily dose may be administered in 1 mg, 5 mg, 6.25 mg, 10 mg, 15 mg, 20 mg, 25 mg, 30 mg, 50 mg, 100 mg, 200 mg, 300 mg, 400 mg, 500 mg, 600 mg, 700 mg or 800 mg dosage forms (Q.D. or B.I.D.). In managing the patient, the therapy may be initiated at a lower dose and increased if necessary as either a single dose or divided doses, depending on the patient's global response. In further embodiments, the daily dose of CFTR potentiator or CFTR corrector is from about 0.01 mg to about 100 mg per kg of a body weight of a patient. In some embodiments, the daily dose of the chosen compound is about 1 mg/kg, 5 mg/kg, 6.25 mg/kg, 10 mg/kg or 25 mg/kg. In certain embodiments, the therapeutically effective amount of the first active agent as provided herein is about 1, 5, or 25 mg per kg of a body weight of the patient per day and the therapeutically effective amount of the additional active agent as provided herein is about 1, 5, or 6.25 mg per kg of a body weight of the patient per day.

The CFTR potentiator and CFTR corrector can be administered before, after, or simultaneously with one of Compound A, Compound A1, Compound A2 or Compound B. The CFTR potentiator or CFTR corrector can be administered before, after, or simultaneously with one of Compound A, Compound A1, Compound A2 or Compound B.

In some embodiments, the CFTR potentiator is ivacaftor, which is administered in a 150 mg oral dose every 12 hours. In some embodiments, the CFTR potentiator is ivacaftor, which is administered in a 250 mg oral dose every 12 hours. In some embodiments, the CFTR corrector is lumacaftor, which is administered in a 400 mg oral dose every 12 hours. In some embodiments, the CFTR corrector is lumacaftor, which is administered in a 600 mg oral dose daily.

In some embodiments, the administration of a combination of one of Compound A, Compound A1, Compound A2 or Compound B in combination with one or more CFTR potentiators and/or one or more CFTR correctors results in a synergistic therapeutic effect for the treatment of CF. In some embodiments, the administration of a combination of one of Compound A, Compound A1, Compound A2 or Compound B and ivacaftor and/or lumacaftor results in a synergistic therapeutic effect for the treatment of CF. In some embodiments, the administration of a combination of one of Compound A, Compound A1, Compound A2 or Compound B and ivacaftor and lumacaftor results in a synergistic therapeutic effect for the treatment of CF. In some embodiments, the administration of a combination of one of Compound A, Compound A1, Compound A2 or Compound B and ivacaftor or lumacaftor results in a synergistic therapeutic effect for the treatment of CF.

Administration of the combinations described herein to a patient can occur simultaneously or sequentially by the same or different routes of administration. In some embodiments, the route of administration is oral in dosage forms of a tablet or a capsule or by inhalation. Particular routes of administration for the agents provided herein are known to those of ordinary skill in the art. See, e.g., *The Merck Manual*, 448 ($17^{th}$ ed., 1999).

4.4. Pharmaceutical Compositions and Dosage Forms

Pharmaceutical compositions can be used in the preparation of individual, single unit dosage forms. Pharmaceutical compositions and dosage forms provided herein may comprise a PDE4 inhibitor, including but not limited to Compound A, Compound A1, Compound A2 or Compound B, or a pharmaceutically acceptable salt, solvate, hydrate, clathrate, or prodrug thereof and one or more CFTR potentiators and/or one or more CFTR correctors as described herein. Pharmaceutical compositions and dosage forms may further comprise one or more carriers, excipients, or diluents.

Single unit dosage forms provided herein are suitable for oral, mucosal (e.g., nasal, sublingual, vaginal, cystic, rectal, preputial, ocular, buccal or aural), parenteral (e.g., subcutaneous, intravenous, bolus injection, intramuscular or intraarterial), topical (e.g., eye drops or other ophthalmic preparations), transdermal or transcutaneous administration to a patient. Non-limiting examples of dosage forms include tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions or a water-in-oil liquid emulsions), solutions and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape and type of dosage forms provided herein will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms provided herein will vary from one another will be readily apparent to those skilled in the art. See, e.g., *Remington's Pharmaceutical Sciences,* 20th ed., Mack Publishing, Easton Pa. (2000).

Typical pharmaceutical compositions and dosage forms comprise one or more excipients. Suitable excipients are well known to those skilled in the art of pharmacy and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients can be accelerated by some excipients such as lactose or when exposed to water. Active ingredients that comprise primary or secondary amines are particularly susceptible to such accelerated decomposition. Consequently, provided herein are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions provided herein may comprise excipients that are well known in the art and are listed, for example, in the *U.S. Pharmacopeia* (USP) 25-NF20 (2002). In general, lactose-free compositions comprise active ingredients, a binder/filler and a lubricant in pharmaceutically compatible and pharmaceutically acceptable amounts. Particular lactose-free dosage forms comprise active ingredients, microcrystalline cellulose, pre-gelatinized starch and magnesium stearate.

Also provided herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, N.Y., NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein may be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Non-limiting examples of suitable packaging include hermetically sealed foils, plastics, unit dose containers (e.g., vials), blister packs and strip packs.

Also provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers or salt buffers. Like the amounts and types of excipients, the amounts and specific types of active ingredients in a dosage form may differ depending on factors such as, but not limited to, the route by which it is to be administered to patients. However, typical dosage forms provided herein comprise either one of (S)—N-(2-(1-(3-ethoxy-4-methoxyphenyl)-2-(methylsulfonyl)ethyl)-1,3-dioxoisoindolin-4-yl)acetamide or (S)—N-(2-(1-(3-ethoxy-4-methoxyphenyl)-2-(methylsulfonyl)ethyl)-3-oxoisoindolin-4-yl)cyclopropanecarboxamide or a pharmaceutically acceptable salt or solvate thereof in an amount of from about 1 to about 1,000 mg. Typical dosage forms comprise one of Compound A, Compound A1, Compound A2 or Compound B, or a pharmaceutically acceptable salt or solvate thereof in an amount of about 1, 2, 5, 7.5, 10, 12.5, 15, 17.5, 20, 25, 30, 50, 100, 150 or 200 mg. In a particular embodiment, a dosage form comprises one of Compound A, Compound A1, Compound A2 or Compound B in an amount of about 1, 5, 10, 15, 20, 25, 30, 50, 100 or 200 mg.

4.4.1. Oral Dosage Forms

Pharmaceutical compositions provided herein that are suitable for oral administration can be presented as discrete dosage forms, such as, but not limited to, tablets (e.g., chewable tablets), caplets, capsules and liquids (e.g., flavored syrups). Such dosage forms contain predetermined amounts of active ingredients and can be prepared by methods of pharmacy well known to those skilled in the art. See generally, *Remington's Pharmaceutical Sciences,* 20th ed., Mack Publishing, Easton Pa. (2000).

Typical oral dosage forms provided herein are prepared by combining the active ingredients in an intimate admixture with at least one excipient according to conventional pharmaceutical compounding techniques. Excipients can take a wide variety of forms depending on the form of preparation desired for administration. Non-limiting examples of excipients suitable for use in oral liquid or aerosol dosage forms include water, glycols, oils, alcohols, flavoring agents, preservatives and coloring agents. Non-limiting examples of excipients suitable for use in solid oral dosage forms (e.g., powders, tablets, capsules and caplets) include starches, sugars, micro-crystalline cellulose, diluents, granulating agents, lubricants, binders and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers or both and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Non-limiting examples of excipients that can be used in oral dosage forms provided herein include binders, fillers, disintegrants and lubricants. Non-limiting examples of binders suitable for use in pharmaceutical compositions and dosage forms include corn starch, potato starch or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose and mixtures thereof.

Non-limiting examples of suitable forms of microcrystalline cellulose include the materials sold as AVICEL-PH-101, AVICEL-PH-103 AVICEL RC-581, AVICEL-PH-105 (available from FMC Corporation, American Viscose Division, Avicel Sales, Marcus Hook, Pa.) and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Non-limiting examples of fillers suitable for use in the pharmaceutical compositions and dosage forms disclosed herein include talc, calcium carbonate (e.g., granules or powder), microcrystalline cellulose, powdered cellulose, dextrates, kaolin, mannitol, silicic acid, sorbitol, starch, pre-gelatinized starch and mixtures thereof. The binder or filler in pharmaceutical compositions is typically present in from about 50 to about 99 weight percent of the pharmaceutical composition or dosage form.

Disintegrants may be used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation and is readily discernible to those of ordinary skill in the art. Typical pharmaceutical compositions comprise from about 0.5 to about 15 weight percent of disintegrant, preferably from about 1 to about 5 weight percent of disintegrant.

Non-limiting examples of disintegrants that can be used in pharmaceutical compositions and dosage forms provided herein include agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums and mixtures thereof.

Non-limiting examples of lubricants that can be used in pharmaceutical compositions and dosage forms provided herein include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laureate, agar and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and mixtures thereof. If used at all, lubricants are typically used in an amount of less than about 1 weight percent of the pharmaceutical compositions or dosage forms into which they are incorporated.

In one embodiment, a solid oral dosage form provided herein comprises either one of Compound A or Compound B, anhydrous lactose, microcrystalline cellulose, polyvinylpyrrolidone, stearic acid, colloidal anhydrous silica and gelatin.

4.4.2. Delayed Release Dosage Forms

Active ingredients can be administered by controlled release means or by delivery devices that are well known to those of ordinary skill in the art. Non-limiting examples of controlled release means or delivery devices include those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556 and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres or a combination thereof to provide the desired release profile in varying proportions. Suitable controlled-release formulations known to those of ordinary skill in the art, including those described herein, can be readily selected for use with the active ingredients provided herein. Thus, in some embodiments, provided herein are single unit dosage forms suitable for oral administration such as, but not limited to, tablets, capsules, gelcaps and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency and increased patient compliance. In addition, controlled-release formulations can be used to affect the time of onset of action or other characteristics, such as blood levels of the drug and can thus affect the occurrence of side (e.g., adverse) effects.

Most controlled-release formulations are designed to initially release an amount of drug (active ingredient) that promptly produces the desired therapeutic effect and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water or other physiological conditions or compounds.

4.4.3. Parenteral Dosage Forms

Parenteral dosage forms can be administered to patients by various routes including, but not limited to, subcutaneous, intravenous (including bolus injection), intramuscular and intraarterial. Because their administration typically bypasses patients' natural defenses against contaminants, parenteral dosage forms are preferably sterile or capable of being sterilized prior to administration to a patient. Non-limiting examples of parenteral dosage forms include solutions ready for injection, dry products ready to be dissolved or suspended in a pharmaceutically acceptable vehicle for injection, suspensions ready for injection and emulsions.

Suitable vehicles that can be used to provide parenteral dosage forms are well known to those skilled in the art. Non-limiting examples of suitable vehicles include Water for Injection USP; aqueous vehicles such as, but not limited to, Sodium Chloride Injection, Ringer's Injection, Dextrose Injection, Dextrose and Sodium Chloride Injection and Lactated Ringer's Injection; water-miscible vehicles such as, but not limited to, ethyl alcohol, polyethylene glycol and polypropylene glycol; and non-aqueous vehicles such as, but not limited to, corn oil, cottonseed oil, peanut oil, sesame oil, ethyl oleate, isopropyl myristate and benzyl benzoate.

Compounds that increase the solubility of one or more of the active ingredients disclosed herein can also be incorporated into the parenteral dosage forms provided herein. For example, cyclodextrin and its derivatives can be used to increase the solubility of either one of (S)—N-(2-(1-(3-ethoxy-4-methoxyphenyl)-2-(methylsulfonyl)ethyl)-1,3-dioxoisoindolin-4-yl)acetamide or (S)—N-(2-(1-(3-ethoxy-4-methoxyphenyl)-2-(methylsulfonyl)ethyl)-3-oxoisoindolin-4-yl)cyclopropanecarboxamide and their derivatives.

4.4.4. Topical and Mucosal Dosage Forms

Drugs can be applied locally to the skin and its adnexa or to a variety of mucous membranes. The routes that can be used include nasal, sublingual, vaginal, cystic, rectal, preputial, ocular, buccal or aural. Many dosage forms have been developed to deliver active principles to the site of application to produce local effects. Non-limiting examples of topical and mucosal dosage forms provided herein include sprays, inhalers, aerosols, ointments, creams, gels, pastes, dusting powders, lotions, liniments, poultices, solutions, emulsions, suspensions, eye drops or other ophthalmic preparations or other forms known to one of skill in the art. See, e.g., *Remington's Pharmaceutical Sciences*, 20th ed., Mack Publishing, Easton Pa. (2000); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms are well known to those skilled in the pharmaceutical arts and depend on the particular tissue to which a given pharmaceutical composition or dosage form will be applied. Non-limiting examples of typical excipients include water, acetone, ethanol, ethylene glycol, propylene glycol, butane-1,3-diol, isopropyl myristate, isopropyl palmitate, mineral oil and mixtures thereof to form solutions, emulsions or gels, which are non-toxic and pharmaceutically acceptable.

Moisturizers such as occlusives, humectants, emollients and protein rejuvenators can also be added to pharmaceutical compositions and dosage forms if desired. Examples of such additional ingredients are well known in the art. See, e.g., *Remington's Pharmaceutical Sciences*, 20th ed., Mack Publishing, Easton Pa. (2000).

Occlusives are substances that physically block water loss in the stratum corneum. Non-limiting examples of occlusives include petrolatum, lanolin, mineral oil, silicones such as dimethicone, zinc oxide and combinations thereof. Preferably, the occlusives are petrolatum and lanolin, more preferably petrolatum in a minimum concentration of 5%.

Humectants are substances that attract water when applied to the skin and theoretically improve hydration of the stratum corneum. However, the water that is drawn to the skin is water from other cells, not atmospheric water. With this type of moisturizer, evaporation from the skin can continue and actually can make the dryness worse. Non-limiting examples of humectants include glycerin, sorbitol, urea, alpha hydroxy acids, sugars and combinations thereof. Preferably, the humectants are alpha hydroxy acids, such as glycolic acid, lactic acid, malic acid, citric acid and tartaric acid.

Emollients are substances that smooth skin by filling spaces between skin flakes with droplets of oil, and are not usually occlusive unless applied heavily. When combined with an emulsifier, they may help hold oil and water in the stratum corneum. Vitamin E is a common additive, which appears to have no effect, except as an emollient. Likewise, other vitamins, for example, A and D, are also added, but their effect is questionable. Non-limiting examples of emollients include mineral oil, lanolin, fatty acids, cholesterol, squalene, structural lipids and combinations thereof.

Protein rejuvenators are substances that rejuvenate the skin by replenishing essential proteins. Non-limiting examples of protein rejuvenators include collagen, keratin, elastin and combinations thereof.

The pH of a pharmaceutical composition or dosage form may also be adjusted to improve delivery of one or more active ingredients. Similarly, the polarity of a solvent carrier, its ionic strength or tonicity can be adjusted to improve delivery. For example, absorption through the skin can also be enhanced by occlusive dressings, inunction or the use of dimethyl sulfoxide as a carrier. Compounds such as metal stearates (e.g., calcium stearate, zinc stearate, magnesium stearate, sodium stearate, lithium stearate, potassium stearate, etc.) can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant and as a delivery-enhancing or penetration-enhancing agent. Different salts, hydrates or solvates of the active ingredients can be used to further adjust the properties of the resulting composition.

In certain embodiments, one or both of the active agents as provided herein are administered parenterally, transdermally, mucosally, nasally, buccally, sublingualy, topically, or orally. In certain embodiments, the first active agent is administered orally in a tablet or capsule form. In certain embodiments, one or more of the active agents are administered topically (e.g. in the dosage form of a lotion or a liquid).

4.4.5. Inhalation Dosage Forms

Also provided herein are dosage forms suitable for delivery of the combinations described herein by inhalation. In some embodiments, the pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

In one embodiment, solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

In one embodiment, the pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

In one embodiment, capsules, blisters and cartridges for use in an inhaler or insufflator may be formulated to contain a powder mix of the pharmaceutical compositions provided herein; a suitable powder base, such as lactose or starch; and a performance modifier, such as L-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

Non-limiting examples of methods of inhalation include PARI-LC nebulizer and eFlow devices. In certain embodiments, Compound A or Compound B are administered in combination with other forms of currently inhaled products for CF patients to augment the function of ivacaftor, e.g., Pulmozyme, TOBI (inhaled tobramycin for inhalation), Cayston, and Hypertonic saline.

4.4.6. Kits

Active ingredients are often not administered to a patient at the same time or by the same route of administration. In some embodiments, provided herein are kits which, when used by the medical practitioner, can simplify the administration of appropriate amounts of active ingredients to a patient.

A typical kit comprises a unit dosage form of one of Compound A, Compound A1, Compound A2 or Compound B, or a pharmaceutically acceptable salt, solvate, hydrate, clathrate, polymorph or prodrug thereof, and a unit dosage form of a second active ingredient, e.g. ivacaftor and/or lumacaftor.

Kits can further comprise devices that are used to administer the active ingredient(s). Examples of such devices include, but are not limited to, syringes, drip bags, patches, and inhalers.

Kits can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Some embodiments provided herein are illustrated by the following non-limiting examples. The examples should not be construed as a limitation in the scope thereof.

5.1. Synthesis of 2-[1-(3-ethoxy-4-methoxyphenyl)-2-methylsulfonylethyl]-4-acetylaminoisoindoline-1,3-dione A stirred solution of 1-(3-ethoxy-4-methoxyphenyl)-methylsulfonylethylamine (1.0 g, 3.7 mmol) and 3-acetamidophthalic anhydride (751 mg, 3.66 mmol) in acetic acid (20 mL) was heated at reflux for 15 h. The solvent was removed in vacuo to yield an oil. Chromatography of the resulting oil yielded the product as a yellow solid (1.0 g, 59% yield): mp, 144° C.; $^1$H NMR (CDCl$_3$) δ1.47 (t, J=7.0 Hz, 3H, CH$_3$), 2.26 (s, 3H, CH$_3$), 2.88 (s, 3H, CH$_3$), 3.75 (dd, J=4.4, 14.3 Hz, 1H, CHH), 3.85 (s, 3H, CH3), 4.11 (q, J=7 Hz, 2H, CH2), 5.87 (dd, J=4.3, 10.5 Hz, 1H, NCH), 6.82-6.86 (m, 1H, Ar), 7.09-7.11 (m, 2H, Ar), 7.47 (d, J=7 Hz, 1H, Ar), 7.64 (t, J=8 Hz, 1H, Ar), 8.74 (d, J=8 Hz, 1H, Ar), 9.49 (br s, 1H, NH); $^{13}$C NMR (CDCl$_3$) δ14.61, 24.85, 41.54, 48.44, 54.34, 55.85, 64.43, 111.37, 112.34, 115.04, 118.11, 120.21, 124.85, 129.17, 130.96, 136.01, 137.52, 148.54, 149.65, 167.38, 169.09, 169.40; Anal Calc'd. for $C_{22}H_{24}NO_7S$: C, 57.38; H, 5.25; N, 6.08. Found: C, 57.31; H, 5.34; N, 5.83.

5.2. Preparation of (+)-2-[1-(3-Ethoxy-4-methoxyphenyl)-2-methylsulfonylethyl]-4-acetylaminoisoindoline-1,3-dione ("Compound A1")

5.2.1. Preparation of 3-Aminophthalic acid

A mixture of 10% Pd/C (2.5 g), 3-nitrophthalic acid (75.0 g, 355 mmol) and ethanol (1.5 L) was charged to a 2.5 L Parr hydrogenator, under a nitrogen atmosphere. Hydrogen was charged to the reaction vessel for up to 55 psi. The mixture was shaken for 13 hours, maintaining hydrogen pressure between 50 and 55 psi. Hydrogen was released and the mixture was purged with nitrogen 3 times. The suspension was filtered through a celite bed and rinsed with methanol. The filtrate was concentrated in vacuo. The resulting solid was reslurried in ether and isolated by vacuum filtration. The solid was dried in vacuo to a constant weight, affording 54 g (84% yield) of 3-aminopthalic acid as a yellow product. $^1$H-NMR (DMSO-d6) δ: 3.17 (s, 2H), 6.67 (d, 1H), 6.82 (d, 1H), 7.17 (t, 1H), 8-10 (brs, 2H). $^{13}$C-NMR (DMSO-d6) δ: 112.00, 115.32, 118.20, 131.28, 135.86, 148.82, 169.15, 170.09.

5.2.2. Preparation of 3-acetamidophthalic anhydride

A 1 L 3-necked round bottom flask was equipped with a mechanical stirrer, thermometer, and condenser and charged with 3-aminophthalic acid (108 g, 596 mmol) and acetic anhydride (550 mL). The reaction mixture was heated to reflux for 3 hours and cooled to ambient temperature and further to 0-5° C. for another 1 hour. The crystalline solid was collected by vacuum filtration and washed with ether. The solid product was dried in vacuo at ambient temperature to a constant weight, giving 75 g (61% yield) of 3-acetamidopthalic anhydride as a white product. $^1$H-NMR (CDCl$_3$) δ: 2.21 (s, 3H), 7.76 (d, 1H), 7.94 (t, 1H), 8.42 (d, 1H), 9.84 (s, 1H).

5.2.3. Resolution of 2-(3-ethoxy-4-methoxyphenyl)-1-(methylsulphonyl)-eth-2-ylamine A 3 L 3-necked round bottom flask was equipped with a mechanical stirrer, thermometer, and condenser and charged with 2-(3-ethoxy-4-methoxyphenyl)-1-(methylsulphonyl)-eth-2-ylamine (137.0 g, 500 mmol), N-acetyl-L-leucine (52 g, 300 mmol), and methanol (1.0 L). The stirred slurry was heated to reflux for 1 hour. The stirred mixture was allowed to cool to ambient temperature and stirring was continued for another 3 hours at ambient temperature. The slurry was filtered and washed with methanol (250 L). The solid was air-dried and then dried in vacuo at ambient temperature to a constant weight, giving 109.5 g (98% yield) of the crude product (85.8% ee). The crude solid (55.0 g) and methanol (440 mL) were brought to reflux for 1 hour, cooled to room temperature and stirred for an additional 3 hours at ambient temperature. The slurry was filtered and the filter cake was washed with methanol (200 mL). The solid was air-dried and then dried in vacuo at 30° C. to a constant weight, yielding 49.6 g (90% recovery) of (S)-2-(3-ethoxy-4-methoxyphenyl)-1-(methylsulphonyl)-eth-2-ylamine-N-acetyl-L-leucine salt (98.4% ee). Chiral HPLC (1/99 EtOH/20 mM KH$_2$PO$_4$ @pH 7.0, Ultron Chiral ES-OVS from Agilent Technologies, 150 mm×4.6 mm, 0.5 mL/min., @240 nm): 18.4 min (S-isomer, 99.2%), 25.5 min (R-isomer, 0.8%).

5.2.4. Preparation of (+)-2-[1-(3-Ethoxy-4-methoxy-phenyl)-2-methylsulfonylethyl]-4-acetylaminoisoin-doline-1,3-dione A 500 mL 3-necked round bottom flask was equipped with a mechanical stirrer, thermometer, and condenser. The reaction vessel was charged with (S)-2-(3-ethoxy-4-methoxyphenyl)-1-(methylsulphonyl)-eth-2-yl amine N-acetyl-L-leucine salt (25 g, 56 mmol, 98% ee), 3-acetamidophthalic anhydride (12.1 g 58.8 mmol), and glacial acetic acid (250 mL). The mixture was refluxed over night and then cooled to <50° C. The solvent was removed in vacuo, and the residue was dissolved in ethyl acetate. The resulting solution was washed with water (250 mL×2), saturated aqueous NaHCO$_3$ (250 mL×2), brine (250 mL×2), and dried over sodium sulphate. The solvent was evaporated in vacuo, and the residue recrystallized from a binary solvent containing ethanol (150 mL) and acetone (75 mL). The solid was isolated by vacuum filtration and washed with ethanol (100 mL×2). The product was dried in vacuo at 60° C. to a constant weight, affording 19.4 g (75% yield) of (S)-{2-[1-(3-ethoxy-4-methoxyphenyl)-2-methylsulfonylethyl]-4-inoisoindoline-1,3-dione with 98% ee. Chiral HPLC (15/85 EtOH/20 mM KH$_2$PO$_4$ @pH 0.5, Ultron Chiral ES-OVS from Agilent Technology, 150 mm×4.6 mm, 0.4 mL/min., @240 nm): 25.4 min (S-isomer, 98.7%), 29.5 min (R-isomer, 1.2%). $^1$H-NMR (CDCl$_3$) δ: 1.47 (t, 3H), 2.26 (s, 3H), 2.87 (s, 3H), 3.68-3.75 (dd, 1H), 3.85 (s, 3H), 4.07-4.15 (q, 2H), 4.51-4.61 (dd, 1H), 5.84-5.90 (dd, 1H), 6.82-8.77 (m, 6H), 9.46 (s, 1H). $^{13}$C-NMR (DMSO-d6) δ: 14.66, 24.92, 41.61, 48.53, 54.46, 55.91, 64.51, 111.44, 112.40, 115.10, 118.20, 120.28, 124.94, 129.22, 131.02, 136.09, 137.60, 148.62, 149.74, 167.46, 169.14, 169.48.

Specific crystalline forms of Compound A may be prepared according to U.S. Pat. No. 7,893,101, the disclosure of which is hereby incorporated by reference in its entirety.

5.3 Preparation of cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide ("Compound B")

5.3.1. Preparation of Methyl 2-methyl-6-nitrobenzoate

A mixture of 2-methyl-6-nitrobenzoic acid (300.0 g, 1.66 moles, from Acros Organics, Morris Plains, N.J.) and trimethyl orthoacetate (298.3 g, 2.48 moles, from Aldrich Chemicals, Milwaukee, Wis.) was charged into a 3-L 3-necked flask at about 20-25° C. under nitrogen. The reaction mixture was gradually heated and the low-boiling point components generated during the reaction were distilled off to an internal temperature of 95-100° C. After 2 hours, the reaction mixture was cooled to 20-25° C. over 1-2 hours. After heptane (1.50 L, from Aldrich Chemicals) was charged into the reaction mixture over 1.0-1.5 hours, the reaction mixture was seeded with methyl 2-methyl-6-nitrobenzoate (0.5 g) when it became turbid. The suspension was cooled to 0-5° C. over 0.5-1 hour and kept at 0-5° C. for another 1.5-2 hours. The solid was collected by filtration under vacuum, washed with heptane (3×300 mL), and dried to a constant weight in a tray at 30-35° C. under a vacuum at 100-120 torr. The yield of methyl 2-methyl-6-nitrobenzoate was 292.0 g (91%), based on 300.0 g of 2-methyl-6-nitrobenzoic acid. The product was found to have a purity of >99% measured by HPLC based on area percentage, and a water content of <0.1% measured by Karl Fisher titration.

5.3.2. Preparation of Methyl 2-bromomethyl-6-nitrobenzoate

A mixture of methyl 2-methyl-6-nitrobenzoate (200.0 g, 1.02 moles, previously prepared), 1,3-dibromo-5,5-dimethylhydantoin (DBH, 162.0 g, 0.57 mole, from Aldrich Chemicals) and methyl acetate (1.20 L, from Aldrich Chemicals) was charged into a 3-L three-necked flask at about 20-25° C. under nitrogen. After the reaction mixture was refluxed for 0.5-1 hour, a solution of 2,2'-azobisisobutyronitrile (AIBN, 8.6 g, 52 mmol, from Aldrich Chemicals) in 100 mL of methyl acetate was charged over 15-30 minutes. The reaction mixture was refluxed for 6.5-8 hours until the amount of unreacted 2-methyl-6-nitrobenzoate was less than 5-10%. The reaction mixture was cooled to 15-18° C. and kept at 15-18° C. for 50-60 minutes. The solid was filtered, washed with cold (i.e., 5-10° C.) methyl acetate (2×100 mL) until there was less than 3% of methyl 2-bromomethyl-6-nitrobenzoate remained in the solid. Next, after heptane (1.00 L) was charged into the filtrate, the upper layer organic phase was washed with 2% of brine (2×500 mL) and deionized water (1-2×500 mL) until there was less than 0.5% (area percentage at 210 nm) of unreacted 5,5-dimethylhydantoin according to measurement by HPLC. After the solution was concentrated under a reduced pressure to remove about 1.80-1.90 L of methyl acetate, methyl tert-butyl ether (MTBE, 300 mL) was charged. After the reaction mixture was refluxed at 65-70° C. for 10-15 minutes, the solution was cooled to 50-55° C. over 0.5-1 hour and seeded with 500 mg of methyl 2-bromomethyl-6-nitrobenzoate at 45-50° C. The suspension was cooled to 20-25° C. and kept at 20-25° C. for 2-3 hours. The solids were collected by filtration, washed with 5-10° C. a cold mixture of heptane and MTBE in a volume ratio of 1:2 (2×100 mL), and dried to a constant weight at 20-25° C. under a vacuum at 100-120 torr. The yield of methyl 2-bromomethyl-6-nitrobenzoate was 185.2 g (66%), based on 200.0 g input of methyl 2-methyl-6-nitrobenzoate. The product was found to have a purity of >98% measured by HPLC based on area percentage, and a water content of <0.1% measured by Karl Fisher titration.

5.3.3. Preparation of (1S)-1-(3-ethoxy-4-methoxyphenyl)-2-methanesulfonyl-ethylamine After a mixture of (1S)-1-(3-ethoxy-4-methoxyphenyl)-2-methanesulfonyl-ethylamine N-acetyl-L-Leucine salt (1.10 kg, 2.46 moles), deionized water (4.40 L), and dichloromethane (DCM, 5.50 L) was charged into a reaction vessel, a solution of sodium hydroxide (196.0 g, 4.90 moles) in 1.00 L of deionized water was charged into the reaction vessel over about 5 minutes at 15-25° C. The resulting mixture was stirred for at least 10 minutes at 15-25° C. and then the aqueous and organic phases were allowed to separate. The pH of the upper aqueous phase was maintained or adjusted at pH 13-14. The phases were separated and the upper aqueous phase was extracted with DCM (2×4.4 L). The pH of the aqueous phase was maintained at 13-14 throughout the extractions. The DCM extracts were combined and washed with deionized water (3.3 L) until the pH of the aqueous phase reached 11 or less. DCM was removed under vacuum below 35° C. The water content of the residual solid should be <0.1% w/w as measured by Karl Fisher titration. The residual solid was dried azeotropically with more DCM. The solid was dried to a constant weight in vacuo at 30-35° C. to give (1S)-1-(3-ethoxy-4-methoxyphenyl)-2-methanesulfonyl-ethylamine as a white powder (639.0-672.0 g, 95-100% yield).

5.3.4. Preparation of (1S)-7-nitro-2-[1-(3-ethoxy-4-methoxyphenyl)-2-(methylsulfonyl)ethyl]isoindolin-1-one (1S)-7-nitro-2-[1-(3-ethoxy-4-methoxyphenyl)-2-(methylsulfonyl)-ethyl]isoindolin-1-one was prepared by the following procedure. A mixture of methyl 2-bromomethyl-6-nitrobenzoate (100.0 g, 365 mmol, prepared previously in Example 6.5.2.), (1S)-1-(3-ethoxy-4-methoxyphenyl)-2-methanesulfonylethylamine (104.7 g, 383 mmol, prepared previously in Example 6.5.3.), sodium hydrogen carbonate (67.5 g, 8.03 moles, from Aldrich Chemicals) and dimethyl formamide (500 mL) was charged into a 1-L 3-necked flask at room temperature under nitrogen. The reaction mixture was gradually heated to an internal temperature of 70-75° C. for two hours until there was less than <2% of unreacted methyl 2-bromomethyl-6-nitrobenzoate. The reaction mixture was gradually heated to an internal temperature of 95-100° C. for 18 hours. The reaction mixture was cooled to 20-25° C. and transferred to an 1-L addition funnel. After purified water (1500 mL) was charged into a 5-L 3-necked flask, the reaction mixture in the addition funnel was added into water in the 5-L 3-necked flask at room temperature over 1-2 hours maintaining an internal temperature below 30° C. The reaction mixture was stirred for 2 hours at room temperature. The solid was filtered out under vacuum, washed with water (3×300 mL) and methanol (2×400 mL), and then charged into a 2-L 3-necked flask followed by methanol (1000 mL). The mixture was refluxed for 1 hour. The mixture was cooled to room temperature. The solid was collected by filtration under vacuum, washed with 200 mL methanol (2 vol), and dried to a constant weight at 40-45° C. under a vacuum at 100-120 torr. The yield of (1S)-7-nitro-2-[1-(3-ethoxy-4-methoxyphenyl)-2-(methylsulfonyl)ethyl] isoindolin-1-one was 123.0 g (78%), based on 100.0 g input of methyl 2-bromomethyl-6-nitrobenzoate. The product was found to have a purity of >99% measured by HPLC based on area percentage, and a water content of <0.1% measured by Karl Fisher titration.

5.3.5. Alternative Preparation of (1S)-7-nitro-2-[1-(3-ethoxy-4-methoxyphenyl)-2-(methylsulfonyl)ethyl]isoindolin-1-one (1S)-7-nitro-2-[1-(3-ethoxy-4-methoxyphenyl)-2-(methylsulfonyl)ethyl]isoindolin-1-one was also prepared by the following procedure. A mixture of methyl 2-bromomethyl-6-nitrobenzoate (100.0 g, 365 mmol, prepared previously in Example 6.5.2.), (1S)-1-(3-ethoxy-4-methoxyphenyl)-2-methanesulfonyl-ethylamine (104.7 g, 383 mmol, prepared previously in Example 6.5.3.), and potassium carbonate powder (100.8 g, 730 mmol, from Aldrich Chemicals) was suspended in acetonitrile (500 mL) at room temperature. The reaction mixture was refluxed at 81-83° C. for about two hours until there was less than 2% of unreacted methyl 2-bromomethyl-6-nitrobenzoate. After the reaction mixture was cooled to 45-50° C., methanol (200 mL) was charged over 5-10 minutes. After the mixture was allowed to cool to 20-25° C. and stirred for 2 hours, deionized water (1.40 L) was charged over 0.5-1 hour and stirred at 20-25° C. for 30 minutes and at 0-5° C. for 1-2 hours. The solid was filtered, washed with deionized water (3×300 mL), and dried to <10% of water content as measured by Karl Fisher titration. The solid was suspended in methanol (750 mL) and refluxed for 1-1.5 hours. The suspension was cooled to 0-5° C. over 1.5-2 hours and kept at 0-5° C. for 1-1.5 hours. The solid was filtered, washed with 0-5° C. methanol (2×200 mL) and heptane (200 mL), and then dried at 40-45° C. under vacuum to a constant weight. The yield of (1S)-7-nitro-2-[1-(3-ethoxy-4-methoxyphenyl)-2-(methylsulfonyl)ethyl]isoindolin-1-one was 148.0 g (93%), based on 100.0 g input of methyl 2-bromomethyl-6-nitrobenzoate. The product was found to have a purity of >99% measured by HPLC based on area percentage, and a water content of <1.0% measured by Karl Fisher titration.

5.3.6. Preparation of Compound B

A mixture of (1S)-7-nitro-2-[1-(3-ethoxy-4-methoxyphenyl)-2-(methylsulfonyl)ethyl]isoindolin-1-one (60 g, 138 mmol, prepared previously in Example 6.5.5.), 10% Pd/C (50% wet, 2.4 g, 4 wt %, from Johnson Matthey, London, UK), ethyl acetate (780 mL) was charged into a Parr-vessel at room temperature under nitrogen. After the mixture was purged with nitrogen three times and with hydrogen three times, the reaction mixture was heated to 40° C. and then the heat was removed. The reaction mixture was stirred with hydrogen at a pressure between 40-45 psi over 4-6 hours until there was ≤3% of the hydroxylamine intermediate. The reaction mixture was cooled to 20-25° C. The reaction mixture was filtered through a celite bed (1 inch thickness) and then bed-washed with ethyl acetate (120 mL). The filtrate was transferred to a 3-L 3-necked flask equipped with a 50-mL addition funnel. After N,N-diisopropylethylamine (29 mL, 165 mmol) was charged into the flask, the addition funnel was charged with cyclopropylcarbonyl chloride (13.0 mL, 145 mmol, from Aldrich Chemicals). The cyclopropylcarbonyl chloride was added at room temperature over 1-2 hours at an internal temperature below 30° C. The reaction mixture was stirred for 2-4 hours at room temperature. After heptane (300 mL) was added, the reaction mixture was stirred for 4-6 hours. The solid was collected by filtration under vacuum, washed with 2N HCl (2×300 mL), water (2×300 mL) and then heptane (2×300 mL). The crude product was dried at 40-45° C. under a vacuum at 100-120 torr to a constant weight. The yield of crude Compound B was 58 g (88%), based on 60.0 g input of (1S)-7-nitro-2-[1-(3-ethoxy-4-methoxyphenyl)-2-(methylsulfonyl)ethyl]-isoindolin-1-one.

5.3.7. Recrystallization of Compound B

A mixture of crude Compound B (95.2 g, prepared previously in Example 6.5.6.) and tetrahydrofuran (THF, 1.43 L) was charged into a 3 L flask at 20-25° C. under nitrogen. The suspension was heated to 60-65° C. until dissolution was achieved. The suspension was filtered at 45-50° C. and the solid was rinsed with 95 mL of THF prewarmed at 45-55° C. After about 950-1150 mL of THF was distilled off at normal pressure over 30-60 minutes, absolute ethanol (950 mL) was charged at 55-60° C. over 5-10 minutes. About 350-400 mL of solvents was removed at normal pressure until the internal temperature rose to 72-74° C. The resulting suspension was refluxed at 72-75° C. for 30-60 minutes, cooled to 20-25° C. over 1-2 hours and kept at 20-25° C. for another 1-2 hours. The solid was collected by filtration under vacuum, washed with absolute ethanol (240-280 mL) and heptane (240-280 mL), and then dried in tray at 50-55° C. in vacuo at 130-140 torr to a constant weight. The yield of the off-white crystalline product was (88.0-91.0 g, 92-96%).

The compounds described herein may also be prepared according to the process described in U.S. Patent Publication No. 2010/0168475, the disclosure of which is hereby incorporated by reference in its entirety.

5.4 Inhibition of PDE4

Phosphodiesterase 4 enzyme was purified from U937 human monocytic cells by gel filtration chromatography, and phosphodiesterase reactions were carried out as previously described. See, e.g., Muller et al., *Bioorg. Med. Chem. Lett.*, 1998, 8(19): 2669-2674. Briefly, reactions were carried out in 96-well deep-well plates in 50 mM Tris HCl pH 7.5, 5 mM $MgCl_2$, 1 µM cyclic adenosine monophosphate (cAMP), plus 10 nM [$^3$H]-cAMP for 45 min at 30° C. The reactions were terminated by boiling, treated with 1 mg/ml snake venom, and separated using AG-1X8 ion exchange resin (BioRad). Reactions consumed less than 15% of available substrate. Compound A1 inhibited PDE4 with an $IC_{50}$ of 73.5 nM. Compound B inhibited PDE4 with an $IC_{50}$ of 100 nM.

5.5. Evaluation of the Activity of Drug Combinations in Human Primary Bronchial Epithelial Cells from CF Patients Human primary bronchial epithelial cells from a CF patient homozygous for delF508, G551D, and/or other mutations are obtained. The platform used is the Ussing chamber, which provides a read-out that is a close correlate with clinical function of CFTR, and has known responsiveness to ivacaftor and forskolin.

Initial experiments are conducted with a single donor of CF HBE (delF508/delF508). Cells are grown on transwell inserts and differentiated for 21 to 28 days prior to the assessment of trans-epithelial chloride flux. A total of six replicates are run. The experiment is split into 3 runs. All experiments are performed with cells grown just prior to the experiment at low temperature (~27° C.) to allow correction of the trafficking defect of delF508 CFTR:

1) Experiment to Determine the 20% Effective Concentration ($EC_{20}$) of Forskolin (Fsk):
   ivacaftor added to 12 Transwell inserts (TW)
   Six TW run with a forskolin titration (1 nM to 100 uM)
   Six TW run with the solvent control DMSO
2) Experiment to Determine the $EC_{max}$ of Ivacaftor:
   Six TW run with $EC_{20}$ fsk+titration of ivacaftor
   Six TW run with $EC_{20}$ fsk+DMSO
3) Experiment to Determine PDE4 Inhibitor Effect ($EC_{max}$ Determination)
   Six TW run with $EC_{20}$ fsk+$EC_{max}$ ivacaftor+titration of Compound A, Compound A1, Compound A2 or Compound B
   Six TW run with $EC_{20}$ fsk+$EC_{max}$ ivacaftor+DMSO The embodiments described above are intended merely to be exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating cystic fibrosis, which comprises administering to a patient in need of such treatment (i) a therapeutically effective amount of a first active agent which is a compound of formula (III):

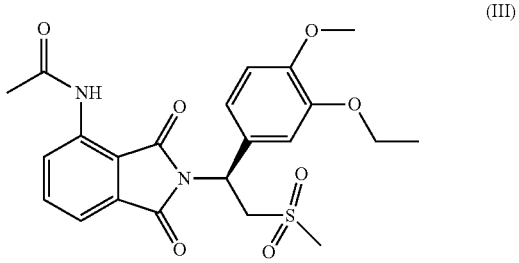 [SMILES: CCOc1cc([C@@H](CS(C)(=O)=O)N2C(=O)c3cccc(NC(C)=O)c3C2=O)ccc1OC]

or a pharmaceutically acceptable salt, a pharmaceutically acceptable hydrate, a pharmaceutically acceptable solvate, a pharmaceutically acceptable clathrate, or a pharmaceutically acceptable polymorph thereof, and (ii) a therapeutically effective amount of a cystic fibrosis transmembrane conductance regulator potentiator, a therapeutically effective amount of a cystic fibrosis transmembrane conductance regulator corrector, or a combination thereof.

2. The method of claim 1, which comprises administering to the patient a therapeutically effective amount of the first active agent, a therapeutically effective amount of a cystic fibrosis transmembrane conductance regulator potentiator, and a therapeutically effective amount of a cystic fibrosis transmembrane conductance regulator corrector.

3. The method of claim 1, wherein the cystic fibrosis transmembrane conductance regulator potentiator is ivacaftor.

4. The method of claim 1, wherein the cystic fibrosis transmembrane conductance regulator corrector is lumacaftor.

5. The method of claim 1, wherein the therapeutically effective amount of the first active agent is about 1, 5, 10, 15, 20, 25, 30, 50, 100, 200, or 300 mg per day.

6. The method of claim 1, wherein one or more of the active agents are administered orally.

7. The method of claim 1, wherein the first active agent is administered orally in a tablet or capsule form.

8. The method of claim 3, wherein ivacaftor is administered orally in an amount of 150 mg twice per day.

9. The method of claim 3, wherein ivacaftor is administered orally in an amount of 250 mg twice per day.

10. The method of claim 4, wherein lumacaftor is administered orally in an amount of 400 mg twice per day.

11. The method of claim 4, wherein lumacaftor is administered orally in an amount of 600 mg per day.

12. The method of claim 1, wherein one or more of the active agents are administered by inhalation.

13. The method of claim 1, wherein the patient exhibits the G551D mutation in the cystic fibrosis transmembrane conductance regulator gene.

14. The method of claim 1, wherein the patient exhibits the delF508 mutation in the cystic fibrosis transmembrane conductance regulator gene.

15. The method of claim 1, wherein the patient exhibits the R117H mutation in the cystic fibrosis transmembrane conductance regulator gene.

16. The method of claim 2, wherein said CFTR potentiator comprises ivacaftor, and said CFTR corrector comprises lumacaftor.

17. A method of treating cystic fibrosis, which comprises administering to a patient in need of such treatment (i) a therapeutically effective amount of a compound of formula (III):

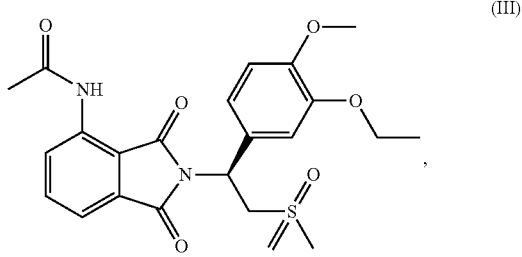 [SMILES: C=S(C)(=O)C[C@H](c1ccc(OC)c(OCC)c1)N1C(=O)c2cccc(NC(C)=O)c2C1=O]

a pharmaceutically acceptable salt, a pharmaceutically acceptable hydrate, a pharmaceutically acceptable solvate, a pharmaceutically acceptable clathrate, or a pharmaceutically acceptable polymorph thereof, (ii) a therapeutically effective amount of ivacaftor, and (iii) a therapeutically effective amount of lumacaftor.

* * * * *